(12) United States Patent
Vaughan et al.

(10) Patent No.: US 10,758,350 B2
(45) Date of Patent: Sep. 1, 2020

(54) TRANSCATHETER PROSTHETIC HEART VALVE DELIVERY SYSTEM WITH PROTECTIVE FEATURE

(71) Applicant: Medtronic Vascular, Inc., Santa Rosa, CA (US)

(72) Inventors: Brendan Vaughan, Clare (IE); Maeve Britton, Galway (IE); Martha Barajas-Torres, Santa Rosa, CA (US); Susheel Deshmukh, Santa Rosa, CA (US); Leonel Mendoza, Santa Rosa, CA (US); Siyan Som, Fulton, CA (US); Michele Silver, Healdsburg, CA (US); Don Tran, Novato, CA (US); Nathan Brown, Santa Rosa, CA (US); Jill Mendelson, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 371 days.

(21) Appl. No.: 15/614,479

(22) Filed: Jun. 5, 2017

(65) Prior Publication Data

US 2017/0348101 A1 Dec. 7, 2017

Related U.S. Application Data

(60) Provisional application No. 62/345,957, filed on Jun. 6, 2016.

(51) Int. Cl.
*A61F 2/24* (2006.01)
*A61F 2/95* (2013.01)

(52) U.S. Cl.
CPC .......... *A61F 2/2436* (2013.01); *A61F 2/2439* (2013.01); *A61F 2/95* (2013.01);
(Continued)

(58) Field of Classification Search
CPC ...... A61F 2/2427; A61F 2/243; A61F 2/2433; A61F 2/2436; A61F 2/2439; A61F 2/95;
(Continued)

(56) References Cited

U.S. PATENT DOCUMENTS

| 2011/0257733 A1 | 10/2011 | Dwork |
| 2012/0277845 A1* | 11/2012 | Bowe .................. A61F 2/95 623/1.11 |

(Continued)

FOREIGN PATENT DOCUMENTS

| DE | 10 2008 014730 A1 | 9/2008 |
| WO | WO 2009/091509 A1 | 7/2009 |

(Continued)

OTHER PUBLICATIONS

PCT International Search Report dated Jan. 23, 2018 in corresponding PCT Appln. No. PCT/US2017/036077.

*Primary Examiner* — Diane D Yabut
(74) *Attorney, Agent, or Firm* — Dicke, Billig & Czaja, PLLC

(57) ABSTRACT

Delivery devices for a stented prosthetic heart valve. The delivery device includes a spindle, at least one cord, and a covering feature associated with the spindle for selectively covering at least a portion of a stented prosthetic heart valve tethered to the spindle in a delivery state. In some embodiments, the covering feature includes a tip mounted to the spindle. The tip can include an overhang region for selectively covering a portion of the stented prosthetic heart valve. In other embodiments, the tip can include a tip body and a compressible foam bumper. In yet other embodiments, the covering feature includes an outer sheath arranged to selectively cover the stented prosthetic heart valve. The outer sheath can be elastic and stretchable for recapturing a (Continued)

partially expanded prosthesis, for example by including one or more windows covered by a stretchable covering layer.

14 Claims, 11 Drawing Sheets

(52) U.S. Cl.
CPC ..... *A61F 2/2427* (2013.01); *A61F 2002/9534* (2013.01); *A61F 2210/0014* (2013.01); *A61F 2210/0057* (2013.01)

(58) Field of Classification Search
CPC .......... A61F 2/954; A61F 2/958; A61F 2/962; A61F 2002/9505; A61F 2002/9511; A61F 2002/9522; A61F 2002/9534
See application file for complete search history.

(56) References Cited

U.S. PATENT DOCUMENTS

| | | | |
|---|---|---|---|
| 2014/0172067 A1* | 6/2014 | Brown | A61F 2/966 623/1.12 |
| 2015/0066127 A1* | 3/2015 | Johnson | A61F 2/86 623/1.11 |
| 2016/0015543 A1 | 1/2016 | Perouse | |

FOREIGN PATENT DOCUMENTS

| | | |
|---|---|---|
| WO | 2014056754 | 4/2014 |
| WO | WO 2015/184138 A1 | 12/2015 |
| WO | WO 2017/096289 A1 | 6/2017 |

* cited by examiner

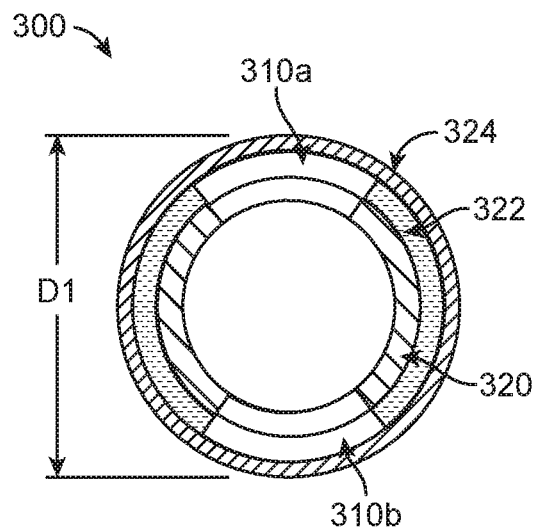
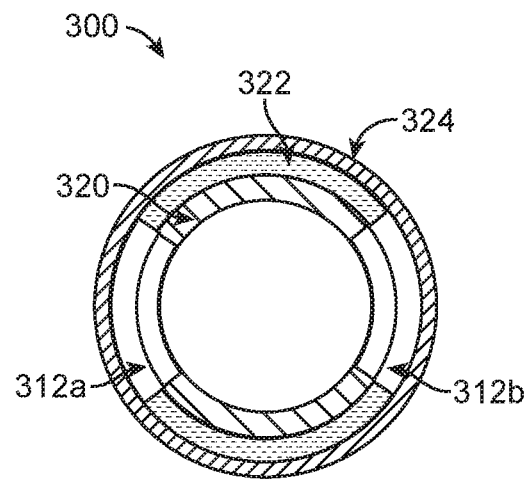
FIG. 14A    FIG. 14B
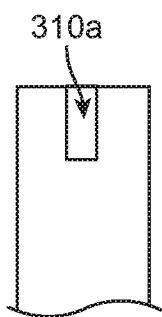
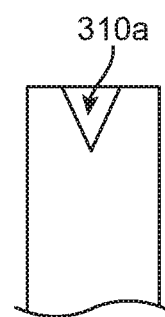
FIG. 15A    FIG. 15B

TRANSCATHETER PROSTHETIC HEART VALVE DELIVERY SYSTEM WITH PROTECTIVE FEATURE

CROSS-REFERENCE TO RELATED APPLICATIONS

This Non-Provisional Patent Application claims the benefit of the filing date of U.S. Provisional Patent Application Ser. No. 62/345,957, filed Jun. 6, 2016, entitled "Transcatheter Prosthetic Heart Valve Delivery System with Protective Feature," the entire teachings of which are incorporated herein by reference.

BACKGROUND

The present disclosure relates to transcatheter stented prosthetic heart valve delivery and deployment. More particularly, it relates to transcatheter delivery systems, devices and methods that guard against vascular damage.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter, inserted inside a body lumen of the patient, such as the femoral artery, and delivered to a desired location in the heart.

The heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. With one type of stented prosthetic heart valve designs, the stent frame is formed to be self-expanding. The valved stent is crimped down to a desired size and held in that compressed state within a sheath or by other means for transluminal delivery. Retracting the sheath (or other release operation) from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

SUMMARY

With some recently considered transcatheter delivery devices and methods, the prosthetic heart valve is compressed and held over a spindle of the device by one or more sutures (or similar material). To deploy the prosthesis, tension in the sutures is slowly released. While viable, these and similar techniques may give rise to undesirable atraumatic contact between portions of the compressed prosthetic heart valve and the patient's vasculature during delivery. In addition, it may be difficult to recapture the prosthetic heart valve relative to the delivery device once tension in the sutures has been released.

The inventors of the present disclosure recognize that a need exists for transcatheter prosthetic heart valve delivery systems and methods that overcome one or more of the above-mentioned problems.

Some aspects of the present disclosure are directed toward delivery devices for a stented prosthetic heart valve. The delivery device includes a spindle, at least one cord, and a covering feature associated with the spindle for selectively covering at least a portion of a stented prosthetic heart valve tethered to the spindle in a delivery state. In some embodiments, the covering feature includes a tip mounted to the spindle. The tip can include an overhang region for selectively covering a portion of the stented prosthetic heart valve. In other embodiments, the tip can include a tip body and a compressible foam bumper. In yet other embodiments, the covering feature includes an outer sheath arranged to selectively cover the stented prosthetic heart valve. The outer sheath can be elastic and stretchable for recapturing a partially expanded prosthesis, for example by including one or more windows covered by a stretchable covering layer.

BRIEF DESCRIPTION OF THE DRAWINGS

FIG. 14A is a cross-sectional view of the sheath of FIG. 13B, taken along the line 14A-14A;

FIG. 14B is a cross-sectional view of the sheath of FIG. 13B, taken along the line 14B-14B;

FIG. 15A is a simplified top view of a portion of the sheath of FIG. 13A;

FIG. 15B is a simplified top view of a portion of another sheath in accordance with principles of the present disclosure;

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Although the present disclosure is described with reference to preferred embodiments, workers skilled in the art will recognize that changes can be made in form and detail without departing from the spirit and scope of the present disclosure.

As described below, some aspects of the present disclosure relate to transcatheter valve delivery devices utilizing one or more flexible cords (e.g., sutures, wires, filaments, etc.) to compress and retain a stented prosthetic heart valve during delivery to a target site. By way of background, stented prosthetic heart valves useful with the delivery devices of the present disclosure can be a bioprosthetic heart valve having tissue leaflets or a synthetic heart valve having polymeric, metallic or tissue-engineered leaflets, and can be specifically configured for replacing any of the four valves of the human heart, or to replace a failed bioprosthesis, such as in the area of an aortic valve or mitral valve, for example.

In general terms, the stented prosthetic heart valves useful with the devices and methods of the present disclosure include a stent or stent frame maintaining a valve structure (tissue or synthetic), with the stent frame having a normal, expanded condition or arrangement and collapsible to a compressed condition or arrangement when loaded to a delivery device. The stent frame is normally constructed to self-deploy or self-expand when released from the delivery device. The stents or stent frames are support structures that comprise a number of struts or wire segments arranged relative to each other to provide a desired compressibility and strength to the prosthetic heart valve. The struts or wire segments are arranged such that they are capable of transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 1A:
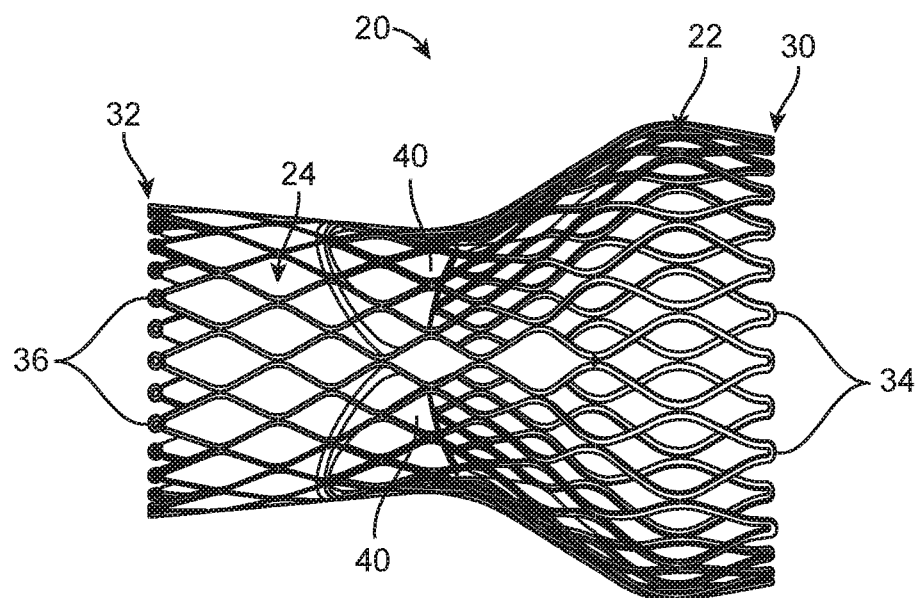
FIG. 1A is a side view of a stented prosthetic heart valve useful with the delivery devices of the present disclosure and in a normal, expanded condition.
Figure 1B:
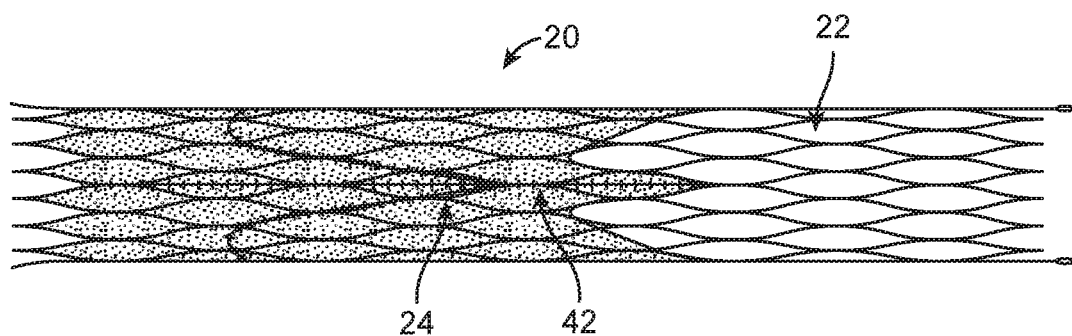
FIG. 1B is a side view of the stented prosthetic heart valve of FIG. 1A in a compressed condition.

With the above understanding in mind, one simplified, non-limiting example of a stented prosthetic heart valve 20 useful with systems, devices and methods of the present disclosure is illustrated in FIG. 1A. As a point of reference, the stented prosthetic heart valve 20 is shown in a normal or expanded condition in the view of FIG. 1A; FIG. 1B illustrates the stented prosthetic heart valve 20 in a compressed condition (e.g., when compressed or cinched to a delivery device as described below). The stented prosthetic heart valve 20 includes a stent or stent frame 22 and a valve structure 24. The stent frame 22 can assume any of the forms mentioned above, and is generally constructed to be self-expandable from the compressed condition (FIG. 1B) to the normal, expanded condition (FIG. 1A). Further, the stent frame 22 defines or terminates at opposing, first and second ends 30, 32. Structural features such as crowns 34, eyelets 36, posts, etc., are formed or carried by the stent frame at one or both of the ends 30, 32.

The valve structure 24 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 24 can be formed, for example, from bovine, porcine, equine, ovine and/or other suitable animal tissues. In some embodiments, the valve structure 24 can be formed, for example, from heart valve tissue, pericardium, and/or other suitable tissue. In some embodiments, the valve structure 24 can include or form one or more leaflets 40. For example, the valve structure 24 can be in the form of a tri-leaflet bovine pericardium valve, a bi-leaflet valve, or another suitable valve. In some constructions, the valve structure 24 can comprise two or three leaflets that are fastened together at enlarged lateral end regions to form commissural joints, with the unattached edges forming coaptation edges of the valve structure 24. The leaflets 40 can be fastened to a skirt that in turn is attached to the frame 22. The side-by-side arrangement of the leaflets 40 establishes commissures 42, one of which is identified in FIG. 1B.

With the one exemplary construction of FIGS. 1A and 1B, the stented prosthetic heart valve 20 can be configured (e.g., sized and shaped) for replacing or repairing an aortic valve. Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve). Thus, in the various delivery device embodiments described below, where reference is made to the stented prosthetic heart valve (or prosthesis) 20, a shape of the prosthesis 20 is generically illustrated, reflecting that the prosthesis 20 can assume any shape in the normal, expanded condition.

Figure 2:
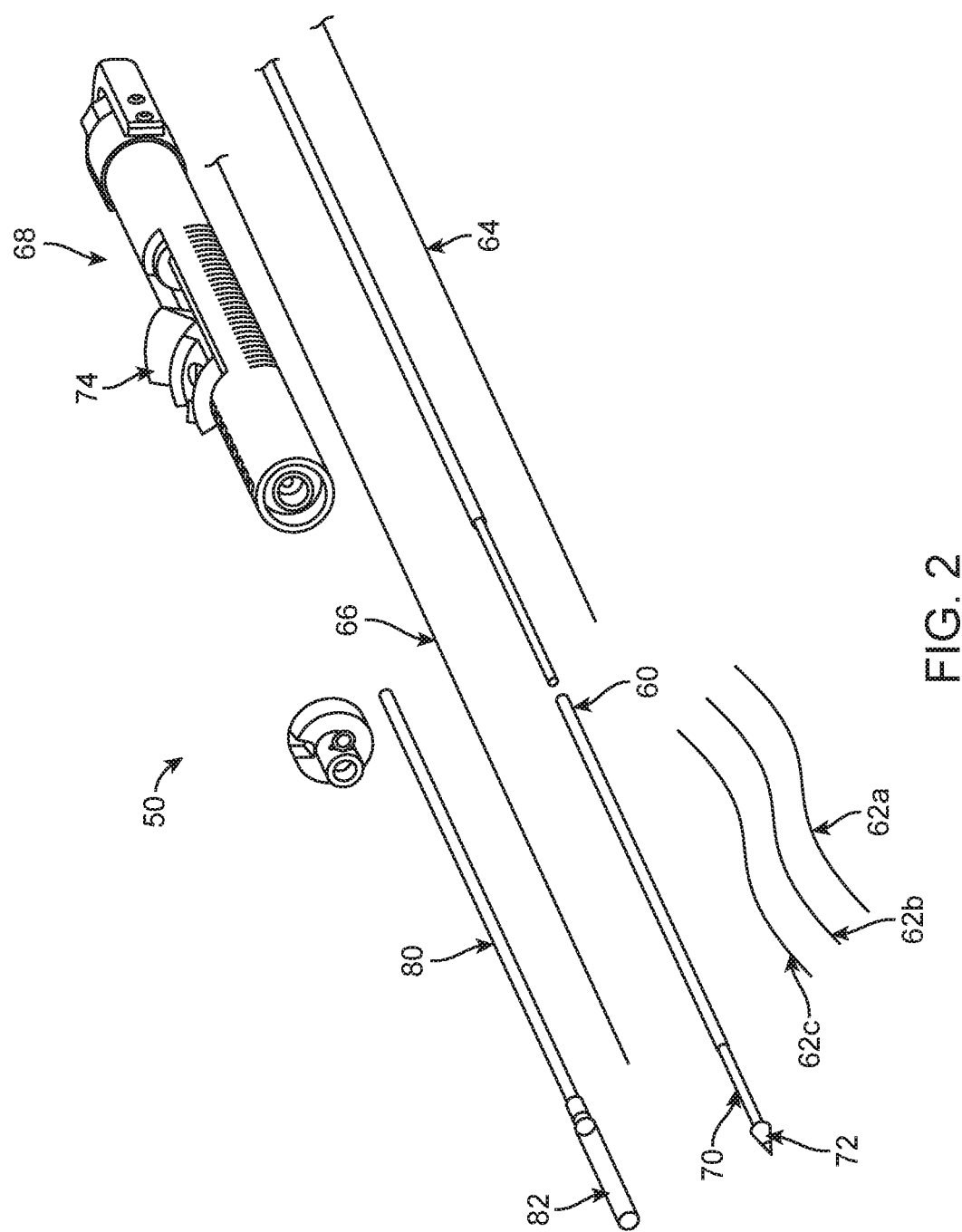
FIG. 2 is a perspective, exploded view of components of a delivery device in accordance with principles of the present disclosure.

By way of further background, FIG. 2 illustrates one non-limiting example of general components of a delivery device 50 with which some embodiments of the present disclosure are useful. The delivery device 50 includes an inner shaft 60, a plurality of cords (such as cords 62a-62c), an optional tension control rod 64, an optional release pin 66, and a handle assembly 68. The inner shaft 60 extends from the handle assembly 68 and includes or carries a spindle 70 connected to a tip 72. One or more lumens (not shown) are defined in the inner shaft 60 (and extend to the spindle 70). The tension control rod 64 is connected to the handle assembly 68 and is slidably disposed within one of the lumens of the inner shaft 60. As described in greater detail below, the cords 62a-62c (e.g., sutures, wires, filaments, etc.) are each coupled at a fixed end thereof to the tension control rod 64, and extend through the inner shaft 60. Where provided, the release pin 66 is also connected to the handle assembly 68, and is slidably disposed within another lumen of the inner shaft 60 for selectively engaging and releasing a free end of the each of the cords 62a-62c. The handle assembly 68 includes one or more actuators 74 for user-prompted longitudinal movement of the tension control rod 64 and of the release pin 66 relative to each other and relative to the inner shaft 60. The handle assembly 68 can incorporate addition control mechanisms actuating other optional components of the delivery device 50. For example, an outer sheath assembly 80 is optionally provided, forming a capsule 82 that can be slidably disposed over the inner shaft 60.

Figure 3:
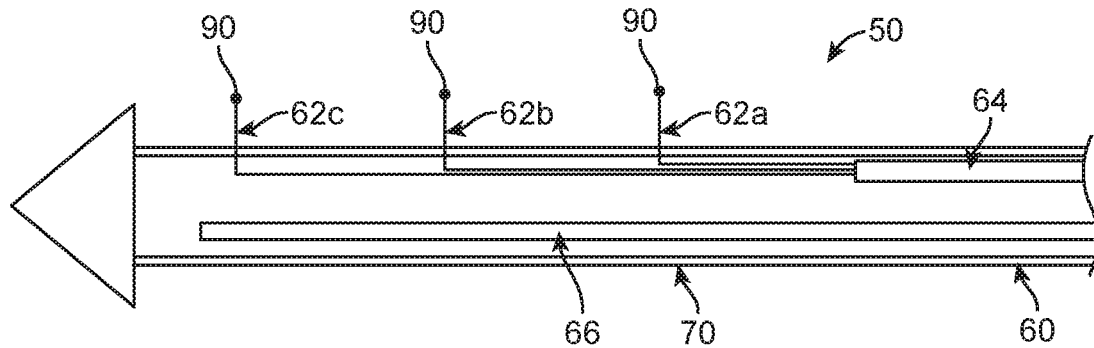
FIG. 3 is a simplified cross-sectional view of a portion of the delivery device of FIG. 2 upon final assembly.

Assembly of the delivery device 50 is generally reflected by the simplified cross-sectional representation of FIG. 3. As a point of reference, for ease of illustration, individual lumens formed within the inner shaft spindle 70 are not shown in FIG. 3 or in any other simplified cross-sectional representation of the present disclosure. The tension control rod 64 is connected to a fixed end of the each of the cords 62a-62c. The cords 62a-62c are flexible and substantially inextensible bodies (e.g., sutures, wires, filaments, etc.). The cords 62a-62c extend from the tension control rod 64, and individually pass through a respective hole or port (not shown) in the spindle 70. As identified in FIG. 3, each of the cords 62a-62c terminates at a free end 90. With embodiments in which three of the cords 62a-62c are provided, relative to the arrangement of FIG. 3, the first cord 62a serves as a proximal cord, the second cord 62b serves as an intermediate cord, and the third cord 62c serves as a distal cord. In other embodiments, more or less than three of the cords 62a-62c can be included with the delivery device 50.

The optional release pin 66 is slidably disposed within a separate lumen of the spindle 70 for reasons made clear below.

Figure 4A:
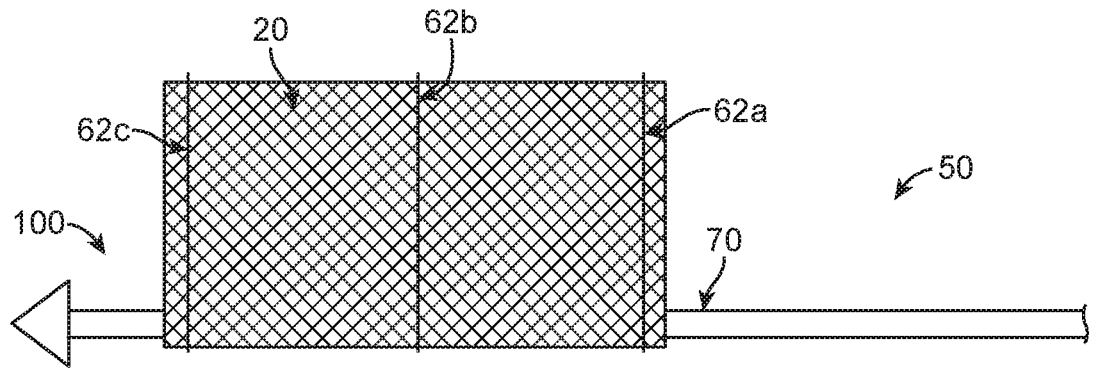
FIG. 4A is a simplified side view of a stented prosthetic heart valve and the delivery device of FIG. 2 in a tethered and expanded state.
Figure 4B:
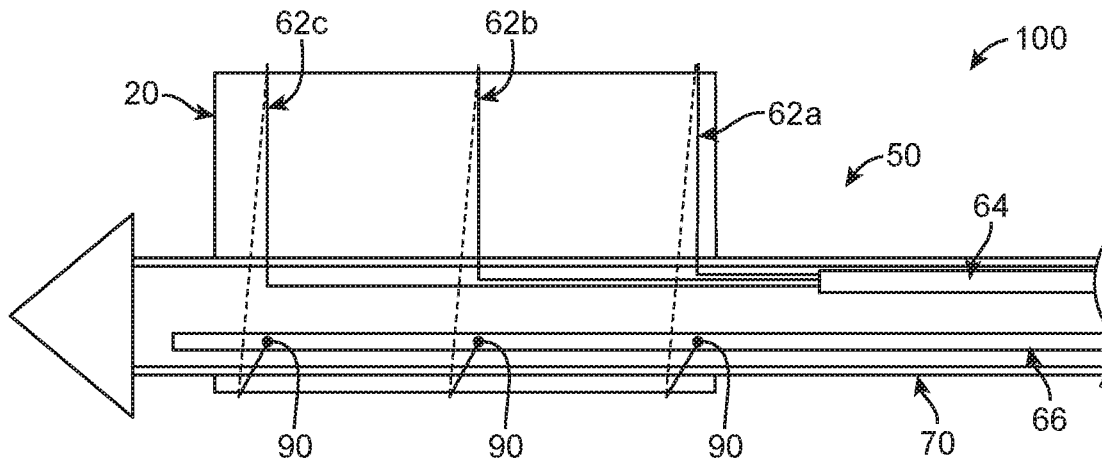
FIG. 4B is a simplified cross-sectional view of the arrangement of FIG. 4A.

FIGS. 4A and 4B illustrate, in simplified form, the stented prosthetic heart valve 20 as initially loaded to the delivery device 50. A length of each of the cords 62a-62c extending from the tension control rod 64 wraps about or engages a circumference of the prosthesis 20. The free end 90 of each of the cords 62a-62c is directed into the spindle 70 and brought into engagement with the release pin 66 (e.g., the free end 90 can from a loop that slidably receives the release pin 66). Alternatively, the release pin 66 can be omitted, with the free end 90 being routed through the inner shaft 60 and back to the handle assembly 68 (FIG. 2). Once connected, the stented prosthetic heart valve 20 and the delivery device 50 collectively define a system 100.

Figure 5A:
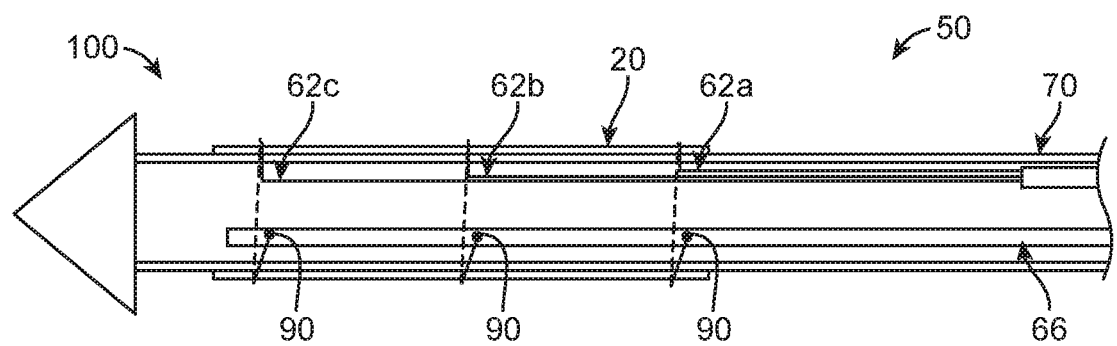
FIG. 5A is a simplified cross-sectional view of the components of FIG. 4A in a delivery state, including the stented prosthetic heart valve cinched to a compressed condition.
Figure 5B:
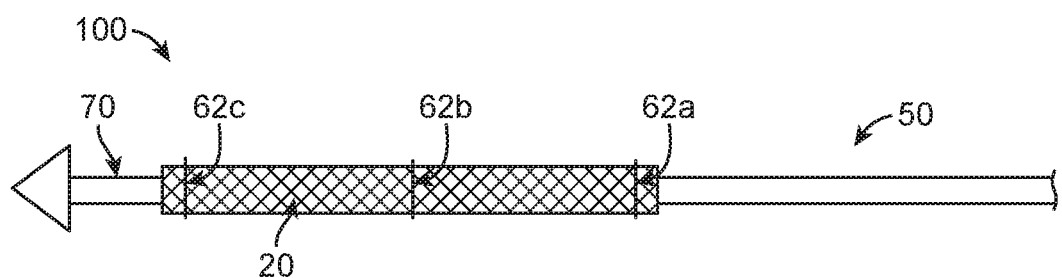
FIG. 5B is a simplified side view of the arrangement of FIG. 5A.
Figure 6:
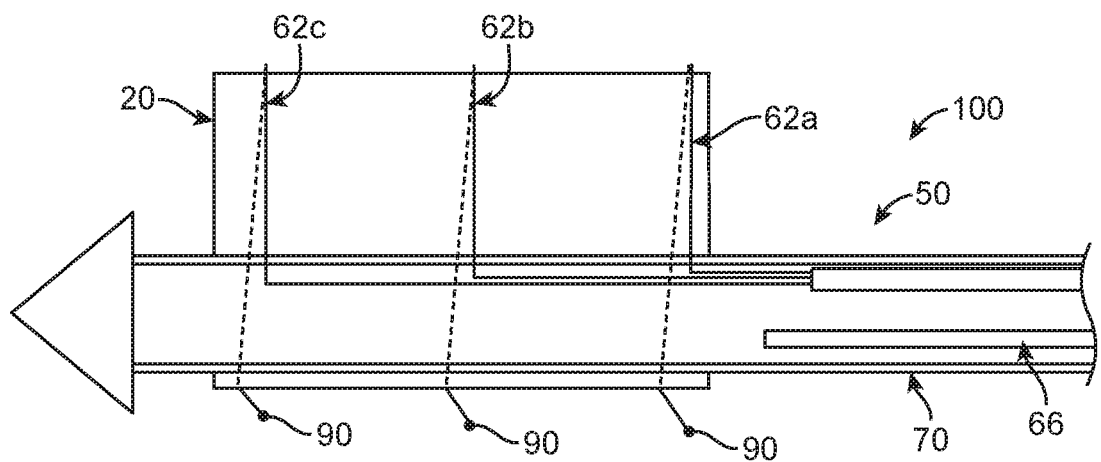
FIG. 6 is a simplified side view of the components of FIG. 4A and illustrating complete deployment of the stented prosthetic heart valve from the delivery device.

The stented prosthetic heart valve 20 can then be compressed or cinched onto the spindle 70 by proximally retracting the tension control rod 64 as reflected in the simplified view of FIGS. 5A and 5B. The release pin 66, and thus the free end 90 of each of the cords 62a-62c engaged therewith, remains stationary during proximal movement of the tension control rod 64. Thus, proximal retraction of the tension control rod 64 tensions the cords 62a-62c and shortens the length of each cord 62a-62c outside of the spindle 70, in turn forcing the prosthesis 20 to radially collapse or compress. FIGS. 5A and 5B represented a delivery state of the system 100 (in which the prosthesis 20 has been compressed or cinched onto the delivery device 50). In the delivery state, the system 100 is manipulated to deliver the prosthetic heart valve 20 via the patient's vasculature (or other percutaneous approach). Once the delivery device 50 has been directed to locate the prosthetic heart valve 20 at the targeted native valve site, the tension control rod 64 can be distally advanced relative to the spindle 70 back toward the arrangement of FIGS. 4A and 4B. Proximal advancement of the tension control rod 64 releases tension in the cords 62a-62c, allowing the prosthesis 20 to self-expand to or toward the normal, expanded condition reflected by the views. Relative to the order of steps, when returned to the arrangement of FIGS. 4A and 4B, the system 100 (i.e, the delivery device 50 and the prosthetic heart valve 20 in combination) is referred to throughout this disclosure as being in a tethered and expanded state (i.e., the prosthetic heart valve 20 has self-reverted to the normal, expanded condition, and remains connected or tethered to the delivery device 50 by the cords 62a-62c). The free end 90 of each of the cords 62a-62c is then released from engagement with the release pin 66 as reflected by FIG. 6 (e.g., where the free ends 90 each are or include a loop slidably received over the release pin 66, the release pin 66 can be proximally retracted until removed from engagement with the free ends 90). The tension control rod 64 can then be proximally retracted, withdrawing the cords 62a-62c from the prosthetic heart valve 20 and into the inner shaft spindle 70. With the prosthesis 20 now fully released, the delivery device 50 can be withdrawn from the patient.

Figure 7:
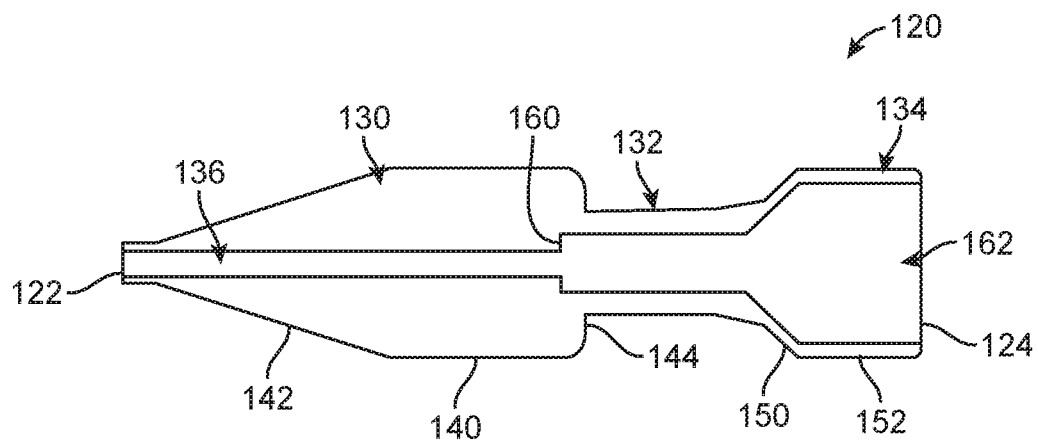
FIG. 7 is a cross-sectional view of a tip in accordance with principles of the present disclosure and useful with the delivery devices of the present disclosure.

With the above in mind, some embodiments of the present disclosure are directed toward delivery device constructions that address possible concerns raised as the system 100, in the delivery state, is tracked through a patient's vasculature. For example, one embodiment of a tip 120 useful with the delivery devices of the present disclosure (e.g., an alternate for the tip 70 of FIG. 2) is shown in FIG. 7. The tip 120 can be an integral, homogenous body extending between opposing, distal and proximal ends 122, 124. An exterior shape of the tip 120 defines a tip region 130, a transition region 132, and an overhang region 134. A central passage 136 extends from, and is open at, the proximal end 124 and is optionally open to the distal end 122.

A shape of the tip region 130 is selected to facilitate atraumatic interface with tissue of a patient akin to conventional catheter tip designs. For example, the tip region 130 can include a trailing section 140 and a leading section 142 extending from the trailing section to 140 to the distal end 122. The trailing section 140 can have a relatively uniform outer diameter. The leading section 142 tapers in outer diameter from the trailing section 140 in a direction of the distal end 122. Thus, an outer diameter of the tip 120 at the distal end 122 is less than an outer diameter of the trialing section 140.

The transition region 132 extends between the tip and overhang regions 130, 134, and is generally configured to robustly maintain a shaft (not shown) as described below. In some embodiments, a radial shoulder 144 is defined at an intersection of the transition region 132 and the trailing section 140 of the tip region 130, generated by an outer diameter of the transition region 132 being less than the outer diameter of the trailing section 140.

The overhang region 134 extends from the transition region 132 to the proximal end 124. A shape of the overhang region 134 defines an inversion section 150 and a cover section 152. The inversion section 150 has an increasing or expanding outer diameter shape or geometry in proximal extension from the transition region 132 to the cover section 152. The cover section 152 can have a relatively uniform outer diameter in extension to the proximal end 124. A wall thickness of the overhang region 134, at least along the cover section 152 and a majority of the inversion section 150, is reduced (as compared to a wall thickness of the transition region 132). The wall thickness, material, and other optional attributes of, or features incorporated into, the overhang region 134 allow the cover section 152 to readily expand in diameter in response to an applied force, and the overhang region 134 to assume an inverted arrangement relative to the transition region 132 as described below.

The central passage 136 can have a relatively uniform diameter along the tip region 130, sized, for example, to slidably receive a guidewire (not shown). A diameter of the central passage 136 along the transition region 132 is greater than the diameter along the tip region 130. The change in diameter defines a lip 160. The change in diameter (and thus the lip 160) can be formed within the tip region 130 as shown. Regardless, the central passage 136 along the transition region 132 is sized, for example, to receive a shaft (not shown), including the shaft abutting the lip 160 as described below. A diameter and shape of the central passage 136 along the overhang region 134 mimics the descriptions above, expanding in the proximal direction from the transition region 132, and being relatively uniform along the cover section 152. The central passage 136 can be viewed as forming a cavity 162 within the overhang region 134.

Figure 8A:
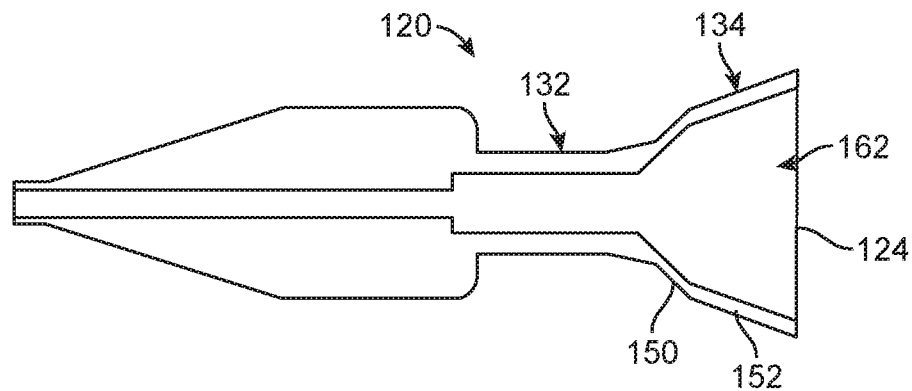
FIG. 8A is a cross-sectional view of the tip of FIG. 7 in a deflected arrangement.

FIG. 7 represents a normal arrangement of the tip 120. Flexibility or deformability of the overhang region 134 can include the overhang region 134 readily increasing in outer diameter in response to an applied force, for example being forced to the deflected arrangement reflected in FIG. 8A by a radially outward force applied to an interior of the overhang region 134 by an external source (not shown). The cover section 152 can be elastically forced to a differing angle relative to the inversion section 150 (as compared to the angle of the normal arrangement of FIG. 7), for example. In the deflected arrangement, a diameter of the cavity 162 increases from the transition region 132 to the proximal end 124. Upon removal of the force, the overhang region 134 self-transitions back to the normal arrangement or shape of FIG. 7. In some embodiments, a material and construction (e.g., wall thickness) of the tip 120 is such that the overhang region 134 is readily forced to, and self-reverts from, a wide variety of deflected shapes. Other features are optionally included that further enhance deformation or flexing of the overhang region 134 to the deflected arrangement, such as a slit, line of weakness, etc.

Figure 8B:
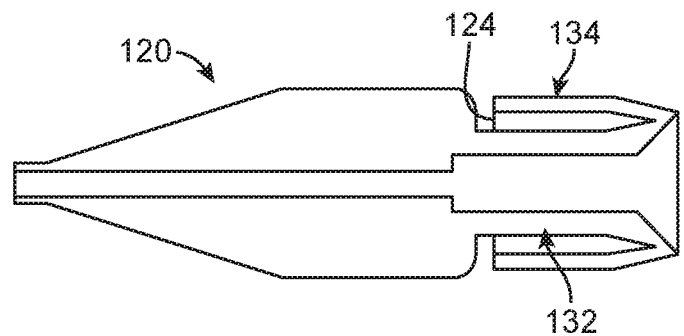
FIG. 8B is a cross-sectional view of the tip of FIG. 7 in an inverted arrangement.

The overhang region 134 can further be reversibly forced from the normal arrangement of FIG. 7 to an inverted arrangement or shape as shown in FIG. 8B. In the inverted arrangement, the overhang region 134 primarily extends in the distal direction over the transition region 132, locating the proximal end 124 proximate the tip region 130. In some embodiments, the tip 120 is configured (e.g., material, geometry, etc.) so that a user can manually "flip" the overhang region 134 from the normal arrangement to the inverted arrangement (and vice-versa). A wall thickness of the transition region 132 can be greater than a wall thickness of the inversion section 150 of the overhang region 134, providing a base against which or relative to which the overhang region 134 can be deflected to and from the inverted arrangement.

A variety of manufacturing techniques can be employed to provide the tip 120 with the elastic deformation characteristics described above. For example, the tip 120 can be formed by an over-molding process in which a material of the tip 120 is molded over a mandrel having a shape corresponding to the central passage 136 as described above (or carrying an insert with the desired shape).

Figure 9A:
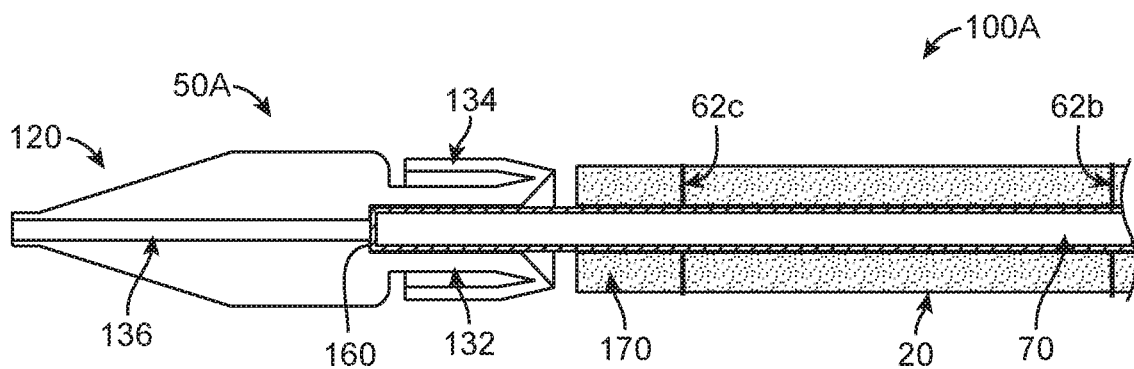
FIG. 9A is a simplified cross-sectional view of a portion of system in accordance with principles of the present disclosure in an initial loading state, the system including a stented prosthetic heart valve and a delivery device, and the delivery device including the tip of FIG. 7.

The above-described, elastically deformable nature of the tip 120, and in particular of the overhang region 134, promotes loading of the stented prosthetic heart valve 20 (FIG. 1) to the delivery device 50 (FIG. 2), and subsequent deployment of the prosthesis 20 from the delivery device 50. For example, FIG. 9A illustrates, in simplified form, a portion of a system 100A including a delivery device 50A and the stented prosthetic heart valve 20 in an initial stage of loading. The delivery device 50A includes the spindle 70 and the tip 120. The spindle 70 is disposed within the central passage 136, optionally abutting the lip 160. The tip 120 can be secured to the spindle 70 via a bond (adhesive, welding, etc.) along the transition region 132. The stented prosthetic heart valve 20 has been disposed over and collapsed or cinched onto the spindle 70 by the cords 62a-62c (two of which are visible in FIG. 9A) as described above with respect to FIGS. 5A and 5B. Prior to collapsing the prosthesis 20 on to the spindle 70, the tip 120 is forced or manipulated to the inverted arrangement as shown. A distal segment 170 of the stented prosthetic heart valve 20 is located slightly proximal the transition region 132. As a point of reference, the distal segment 170 can be either of the prosthesis ends 30, 32 (FIG. 1A), depending upon an orientation of the stented prosthetic heart valve 20 relative to the delivery device 50A. Regardless, the distal segment 170 can include structural features (not shown) of the stent frame 22 (FIG. 1A) such as the crowns 34, eyelets 36, posts, etc. (FIG. 1A) as described above.

Figure 9B:
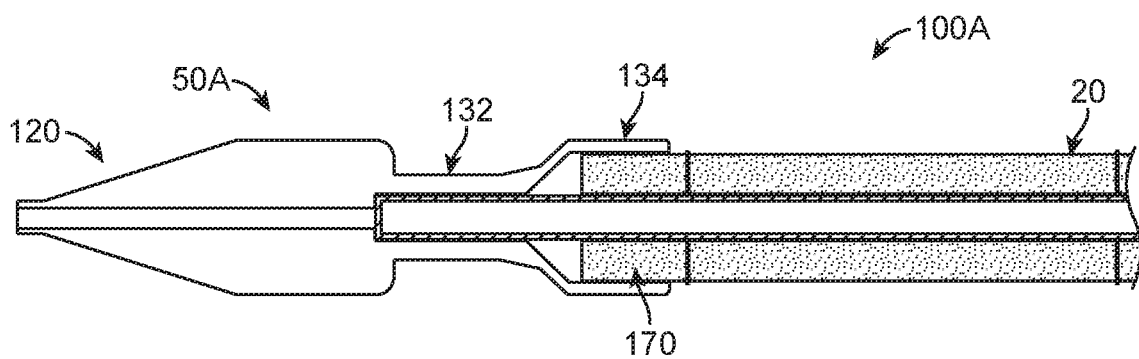
FIG. 9B illustrates the system of FIG. 9A in a delivery state.

Subsequently, the overhang region 134 is returned (e.g., manually manipulated by a user) to the normal arrangement as in FIG. 9B to complete loading of the stented prosthetic heart valve 20. In the delivery state of FIG. 9B, the overhang region 134 overlies the distal segment 170, covering any of the structural features (not shown) carried or formed thereby. In other words, crowns, eyelets, posts, etc., of the distal segment 170 are covered by the overhang region 134.

The system 100A (in the delivery state) is then manipulated to locate the stented prosthetic heart valve 20 at or adjacent a target site (e.g., a native heart valve to be repaired). As the system 100A is tracked through the patient's vasculature, the distal segment 170 remains covered by the overhang region 134, even as the system 100A traverses tight or complex "turns" in the native anatomy. The structural features of the distal segment 170 are never exposed, and thus do not cause damage to the patient's vasculature during delivery. Further, because the distal segment 170 is covered, increased friction forces that might otherwise occur were the distal segment 170 exposed are beneficially avoided.

Figure 9C:
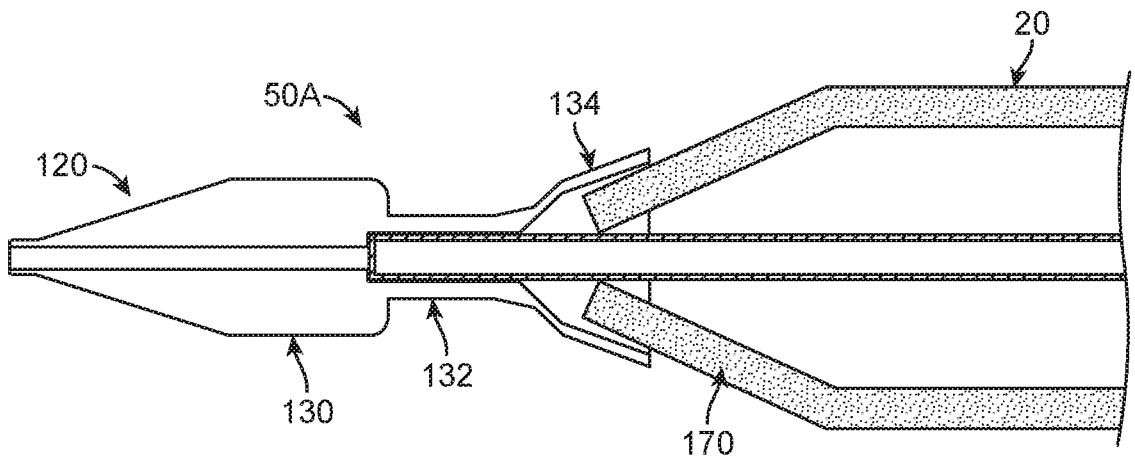
FIG. 9C illustrates the system of FIG. 9B in a deployment state.

Once the stented prosthetic heart valve 20 is desirably located, tension in the cords 62a-62c is then slowly released as described above, allowing the prosthesis 20 to self-revert toward the normal, expanded condition. As stented prosthetic heart valve 20 radially expands, the distal segment 170 exerts a radially outward force on to the overhang region 134. As shown in FIG. 9C, the overhang region 134 readily assumes the deflected arrangement in response to this applied force, allowing the prosthesis 20 to completely release from the tip 120, and thus the delivery device 50A. With the overmold (or similar) design of some embodiments of the present disclosure, an actuator or other mechanism is not required to permit release of the prosthesis 20 from the tip 120.

Figure 10A:
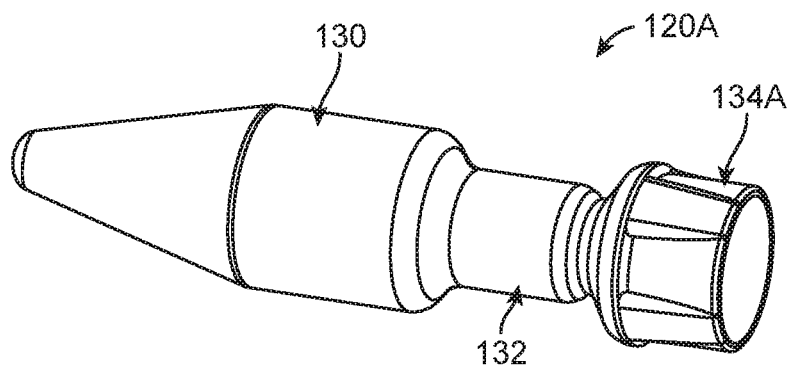
FIG. 10A is a perspective view of another tip in accordance with principles of the present disclosure.
Figure 10B:
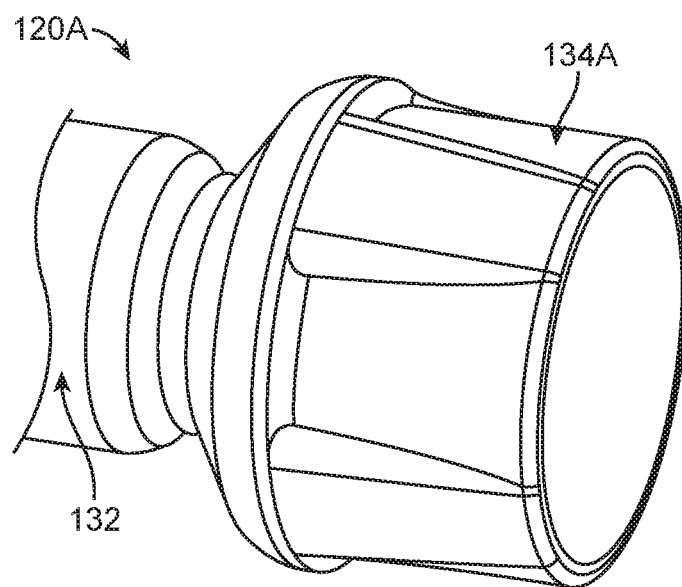
FIG. 10B is an enlarged view of a portion of the tip of FIG. 10A.

While the tip 120 has been described as being an integral, homogeneous body, other constructions can be employed. For example, the tip region 130 and the transition region 132 can be formed as a first body, and the overhang region 134 from as a second body that is assembled to the first body. With this approach, a material (and resulting thickness) of the separately-formed overhang region 134 can differ from that of the tip and transition regions 130, 132 (e.g., the tip and transition regions 130, 132 can be a relatively thick walled molded plastic whereas the overhang region is a thin wall, flexible tube (akin to a sock)). Alternatively or in addition, the overhang region 134 can be formed to have a varying wall thickness. In this regard, another embodiment of a tip 120A in accordance with principles of the present disclosure is shown in FIG. 10A. The tip 120A is akin to the tip 120 (FIG. 7), and include or forms the tip region 130 and the transition region 132 as previously described. An overhang region 134A is also provided, and can be similar to the overhang region 134 (FIG. 7) described above. However, the overhang region 134A can have a varying thickness and incorporate other geometry features as illustrated in FIG. 10B.

Figure 11:
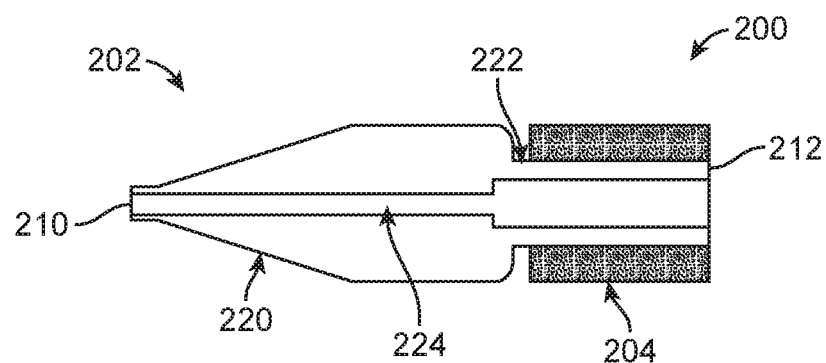
FIG. 11 is a simplified cross-sectional view of another tip in accordance with principles of the present disclosure.

Another embodiment tip 200 in accordance with principles of the present disclosure and useful with delivery devices of the present disclosure (e.g., as the tip 72 of the delivery device 50 of FIG. 2) is shown in simplified form in FIG. 11. The tip 200 includes a tip body 202 and a bumper 204. The tip body 202 can be akin to tips conventionally employed with transcatheter delivery devices (e.g., a molded plastic material), and extends between a distal end 210 and a proximal end 212. The tip body 202 is shaped or formed to define a tip region 220, a transition region 222, and a central passage 224. The tip region 220 can be similar to the tip region 130 (FIG. 7) described above, having a tapering outer diameter in a direction of the distal end 210. The transition region 222 can have a relatively uniform outer diameter in extension from the tip region 220 to the proximal end 212. The central passage 224 extends from, and is open to, the proximal end 212. Commensurate with the above descriptions, the central passage 224 can further be open to the distal end 210, having a diameter along the tip region 220 sized to slidably receive a guide wire (not shown) or similar implement. Along the transition region 222, the central passage 224 can be sized and shaped to receive the spindle 70 (FIG. 2) as described below.

The bumper 204 is disposed or formed over an exterior surface of the transition region 222, and has a deformable or compressible construction. For example, in some embodiments the bumper 204 is a foam material, such as an open cell or closed cell foam. Non-limiting examples of foam materials useful with or as the bumper 204 include a two part polyurethane foam that can be "painted" on the transition region 222, injection molded on to the transition region 222, pour molded on to the transition region 222, etc. Regardless, the bumper 204 is configured to readily radially compress or deform when subjected to an external force.

Figure 12:
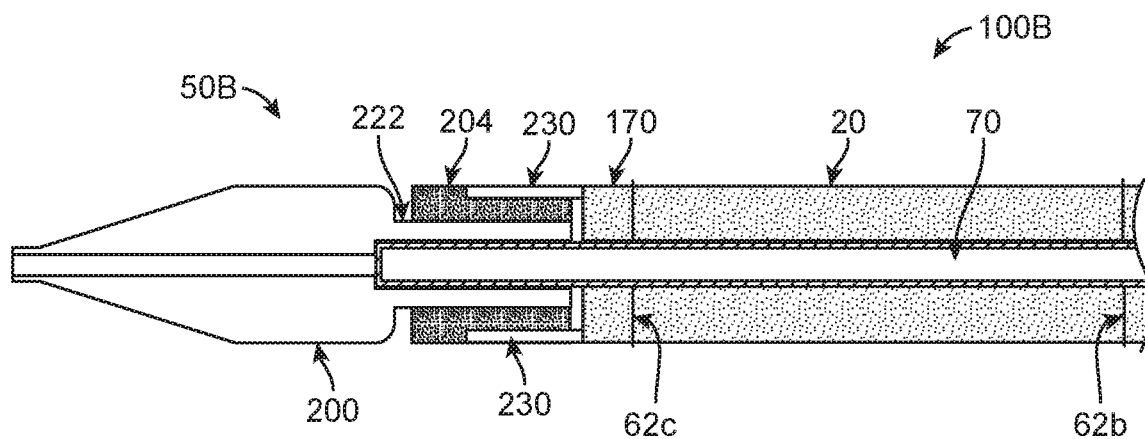
FIG. 12 is a simplified cross-sectional view of a portion of system in accordance with principles of the present disclosure in a delivery state, the system including a stented prosthetic heart valve and a delivery device, and the delivery device including the tip of FIG. 11.

The above-described, compressible nature of the bumper 204 promotes loading of the stented prosthetic heart valve 20 (FIG. 1) to the delivery device 50 (FIG. 2), and subsequent deployment of the prosthesis 20 from the delivery device 50. For example, FIG. 12 illustrates, in simplified form, a portion of a system 100B including a delivery device 50B and the stented prosthetic heart valve 20 in an initial stage of loading. The delivery device 50B includes the spindle 70 and the tip 200. The spindle 70 is disposed within the central passage 224. The tip 200 can be secured to the spindle 70 via a bond (adhesive, welding, etc.) along the transition region 222. The stented prosthetic heart valve 20 has been disposed over and collapsed or cinched onto the spindle 70 by the cords 62a-62c (two of which are visible in FIG. 12) as described above with respect to FIGS. 5A and 5B. A portion of the distal segment 170 of the stented prosthetic heart valve 20 is located to interface with the bumper 204. More particularly, the distal segment 170 includes or terminates in one or more structural features, such as crowns, posts, eyelets, etc. These terminal structural features are represented schematically in FIG. 12 at 230. With collapsing of the stented prosthetic heart valve 20 on to the spindle 70, the structural features 230 embed into the bumper 204, with a material of the bumper 204 compressing or deforming about the structural features 230. Optionally, a cord (not shown) can be routed about the structural features and tightened to further draw the structural features 230 into the bumper 204. Regardless, in the delivery state of FIG. 12, the bumper 204 essentially covers at least a leading edge of the structural features 230.

The system 100B (in the delivery state) is then manipulated to locate the stented prosthetic heart valve 20 at or adjacent a target site (e.g., a native heart valve to be repaired). As the system 100B is tracked through the patient's vasculature, the structural features 230 remain at least partially covered by the bumper 204, even as the system 100B traverses tight or complex "turns" in the native anatomy. At least the leading edge of the structural features 230 is effectively never exposed, and thus do not cause damage to the patient's vasculature during delivery.

Once the stented prosthetic heart valve 20 is desirably located, tension in the cords 62a-62c is then slowly released as described above, allowing the prosthesis 20 to self-revert toward the normal, expanded condition. As stented prosthetic heart valve 20 radially expands, the structural features 230 readily release from the bumper 204, allowing the prosthesis 20 to completely release from the tip 200, and thus the delivery device 50B.

Figure 13A:
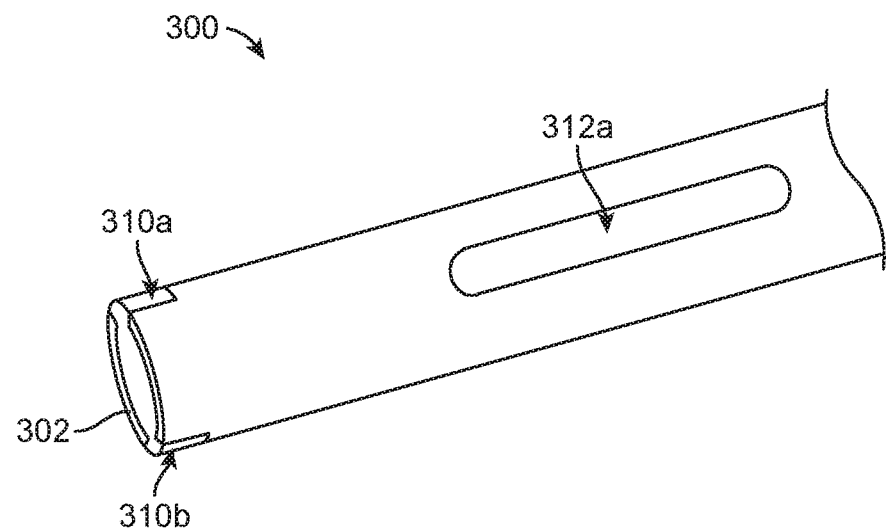
FIG. 13A is a simplified perspective view of a portion of an outer sheath in accordance with principles of the present disclosure and useful with the delivery devices of the present disclosure.

Returning to FIG. 2 and as mentioned above, in some embodiments, the delivery devices of the present disclosure optionally include the outer sheath 80 carrying or forming the capsule 82. Where provided, the outer sheath 80 and the capsule 82 can be configured to selectively cover a loaded and collapsed stented prosthetic heart valve 20 (FIG. 1B) during delivery, as well facilitate recapture of a partially expanded prosthesis. For example, a portion of an outer sheath 300 useful with some delivery devices of the present disclosure (e.g., as the outer sheath 80 and/or the capsule 82) is illustrated in simplified form in FIGS. 13A and 13B. The outer sheath 300 terminates at a distal end 302, and defines a lumen 304. In some embodiments, the outer sheath 300 has a multi-layer construction as described below. Further, the outer sheath 300 can be diametrically expandable or stretchable in certain regions, such as by forming one or more windows. The windows can include one or more distal windows, such as distal windows 310a, 310b, and one or more intermediate windows, such as intermediate windows 312a, 312b (the first intermediate window 312a being visible in the view of FIG. 13A, and the second intermediate window 312b being visible in the view of FIG. 13B).

Figure 13B:
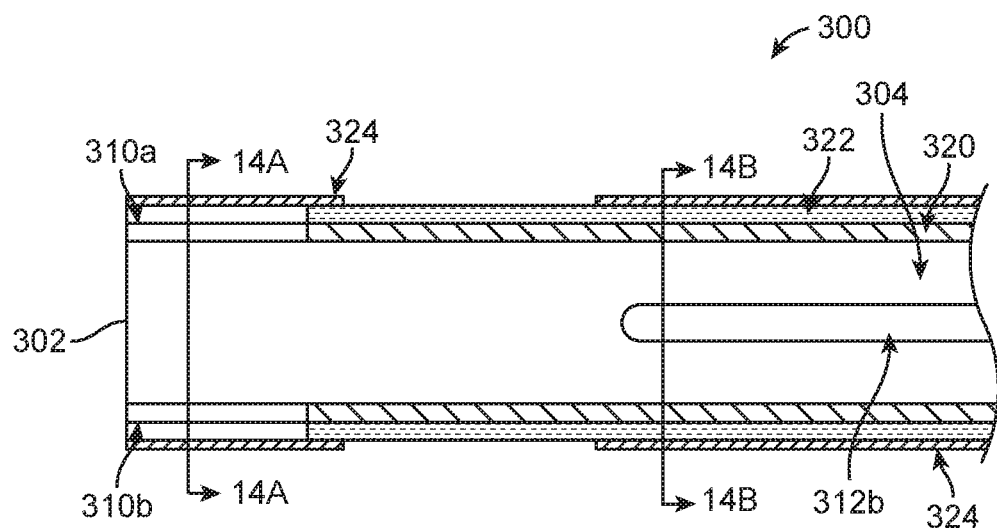
FIG. 13B is a simplified, longitudinal cross-sectional view of a portion of the sheath of FIG. 13A.

With specific reference to FIG. 13B, the multi-layer construction of the outer sheath 300 includes an inner layer 320 and an outer layer 322. The inner and outer layers 320, 322 are both tubular members, with the outer layer 322 being formed over the inner layer 320 (e.g., co-extrusion process). For reasons made clear below, a covering layer 324 is further provided, and can be formed at select regions (e.g., location(s) of the window(s)) or can extend an entire length of the outer sheath 300.

Materials of the inner and outer layers 320, 322 are selected in tandem to provide desired longitudinal rigidity and hoop strength (e.g., appropriate for recapturing a partially expanded stented prosthetic heart valve (not shown)), as well as a low friction surface along the lumen 304 (e.g., appropriate for free sliding movement of a guide wire (not shown) within the lumen 304). For example, the inner layer 320 serves as a liner and can be a thin, low friction plastic material, such as polytetrafluoroethylene (PTFE), or other conventional catheter material or blend of materials. A material or material blend of the outer layer 322 is selected to provide desired hoop strength and longitudinal robustness. In some non-limiting embodiments, the outer layer 322 is or includes a Nylon 12 material, such as Grilamid TR 55™ available from EMS-GRIVORY of Sumter, S.C.

In tubular form, the outer layer 322 is inherently resistant to diametric expansion or stretching. However, where provided, the distal window(s) 310a, 310b impart an expandable or stretchable attribute into the outer sheath 300 at a corresponding distal region 330 of the outer sheath 300 for reasons made clear below. As best shown in FIG. 13B, each of the distal windows 310a, 310b represent an absence of material of, or cut-out through a thickness of, at least the outer layer 322, and optionally of the inner layer 320. With additional reference to FIG. 14A, while two of the distal windows 310a, 310b are illustrated, in other embodiments, a greater or lesser number can be provided. Where two or more are provided, the distal windows 310a, 310b can be uniformly sized and spaced relative to a circumference of the outer sheath 300. In related embodiments, the two distal windows 310a, 310b are diametrically opposed. The distal window(s) 310a, 310b can extend to the distal end 302, and can have the square or rectangular-like shape generally reflected by FIG. 15A. Other shapes are also acceptable, such as triangular (e.g., as in FIG. 15B), complex, etc.

Returning to FIGS. 13A and 13B, where provided, the intermediate window(s) 312a, 312b impart an expandable or stretchable attribute into the outer sheath 300 at a corresponding intermediate region 332 of the outer sheath 300 for reasons made clear below. As shown in FIG. 14B, the optional intermediate windows 312a, 312b represent an absence of material of, or cut-out through a thickness of, at least the outer layer 322 and optionally the inner layer 320. While two of the intermediate windows 312a, 312b are illustrated, in other embodiments a greater or lesser number can be provided. Where two or more are provided, the intermediate windows 312a, 312b can be uniformly sized and spaced relative to a circumference of the outer sheath 300. In related embodiments, the two intermediate windows 312a, 312b are diametrically opposed. A longitudinal length of the intermediate window(s) 312a, 312b is selected to generate desired diametric expandability into the outer sheath 300. For example, where a partially expanded stented prosthetic heart valve (not shown) is to be recaptured and located within the intermediate region 332, a length of the intermediate window(s) 312a, 312b can be increased. With an increased length of the intermediate window(s) 312a, 312b, a minimum diameter of the lumen 304 required for recapturing the prosthesis can be decreased (thus decreasing an overall profile of the outer sheath 300).

Returning to FIGS. 13A and 13B, the outer sheath 300 can include only the distal window(s) 310a, 310b, only the intermediate window(s) 312a, 312b, or both the distal and intermediate window(s) 310a-312b. With the non-limiting example of FIGS. 13A and 13B, the distal windows 310a, 310b are rotationally offset from the intermediate windows 312a, 312b by approximately ninety degrees.

The covering layer 324 is a thin material body extending across each of the windows 310a-312b. In some embodiments, the covering layer 324 is tubular in nature, and can be applied only in regions of the windows 310a-312b; in other embodiments, the covering layer 324 is continuous. Regardless, the covering layer 324 is an elastically stretchable polymer material or material blend (e.g., a thermoplastic polyether-urethane blend, akin to a film. One non-limiting example of a material blend useful as the covering layer 324 is 70% polyether-urethane (e.g., available under the trade designation Elasthane™ from DSM Biomedical Inc. of Berkeley, Calif.), 20% siloxane, and 10% tie resin (e.g., a resin available under the trade designation Plexar® from LyondellBasell Industries of Houston, Tex.). Other materials and material blends are contemplated.

Figure 16:
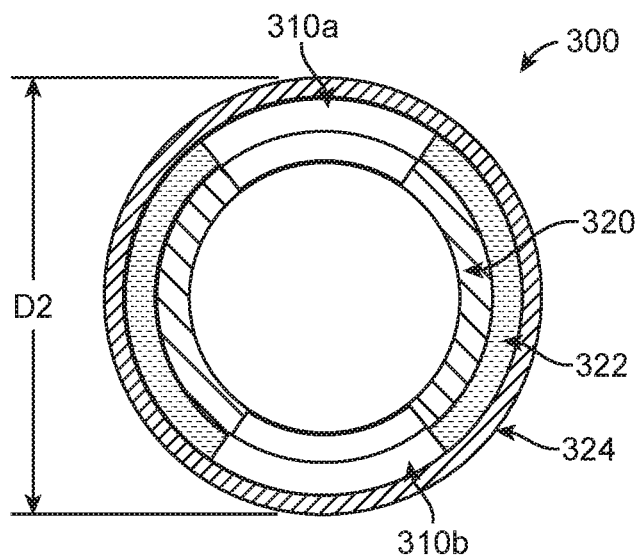
FIG. 16 is the cross-sectional view of FIG. 14A illustrating the sheath in an expanded condition.

The covering layer 324 provides structural integrity to the outer sheath 300 in regions of the window(s) 310a-312b, and maintains this structural integrity while facilitating diametric stretching or expansion. For example, FIG. 14A reflects a normal or un-stretched condition of the outer sheath 300. In response to a radially outward force applied to an interior of the outer sheath 300, the inner and outer layers 320, 322 diametrically (and circumferentially) expand at the distal windows 310a, 310b as reflected by FIG. 16 (i.e., as compared to the condition of FIG. 14A, an arc length of the windows 310a, 310b has increased). Further, the covering layer 324 diametrically (and circumferentially) stretches, and continues to cover the distal windows 310a, 310b thereby maintaining an overall structural integrity of the outer sheath 300 in the expanded condition of FIG. 16. Thus, the outer sheath 300 has an initial diameter D1 (at least at a region of the distal windows 310a, 310b) in the normal condition, and an increased, expanded diameter D2 in the expanded condition.

Figure 17A:
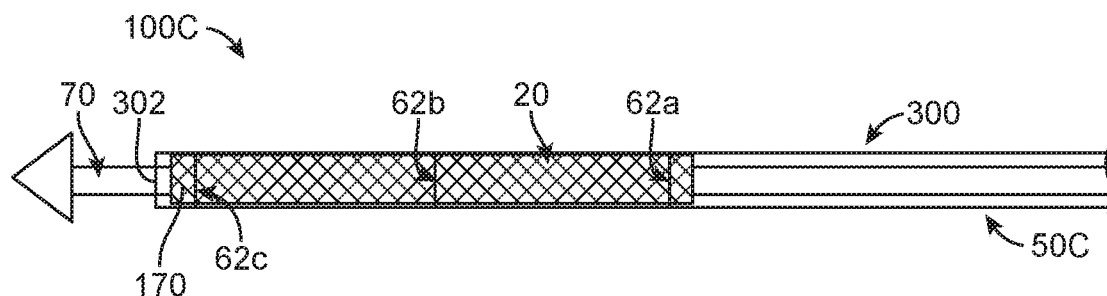
FIG. 17A is a simplified side view of a portion of system in accordance with principles of the present disclosure in a delivery state, the system including a stented prosthetic heart valve and a delivery device, and the delivery device including the outer sheath of FIG. 13A.

The above-described, expandable nature of the outer sheath 300 promotes loading of the stented prosthetic heart valve 20 (FIG. 1) to the delivery device 50 (FIG. 2), and subsequent recapture of prosthesis 20 when partially expanded. For example, FIG. 17A illustrates, in simplified form, a portion of a system 100C including a delivery device 50C and the stented prosthetic heart valve 20 in an initial stage of loading. The delivery device 50C includes cords 62a-62c, the spindle 70 and the outer sheath 300 (drawn transparent in FIGS. 17A and 17B for ease of understanding). The stented prosthetic heart valve 20 has been disposed over and collapsed or cinched onto the spindle 70 by the cords 62a-62c as described above. The outer sheath 300 is advanced distally over the collapsed stented prosthetic heart valve 20 such that the distal end 302 of the outer sheath 300 is distal the distal segment 170 of the prosthesis 20. Thus, any structural features (e.g., crowns, posts, eyelets, etc.) included with or carried by the distal segment 170 are covered or within the outer sheath 300.

The system 100C (in the delivery state) is then manipulated to locate the stented prosthetic heart valve 20 at or adjacent a target site (e.g., a native heart valve to be repaired). As the system 100C is tracked through the patient's vasculature, the distal segment 170 (and the structural features provided therewith) remains covered by the outer sheath 300, even as the system 100C traverses tight or complex "turns" in the native anatomy. The structural features are never exposed, and thus do not cause damage to the patient's vasculature during delivery. Further, with optional embodiments in which the covering layer 324 (FIG. 13B) is provided at the distal region 330 (FIG. 13A) of the outer sheath 300 and includes siloxane or similar material, the siloxane or similar material adds lubricity to the outermost surface of the outer sheath 300 for improved tracking.

Figure 17B:
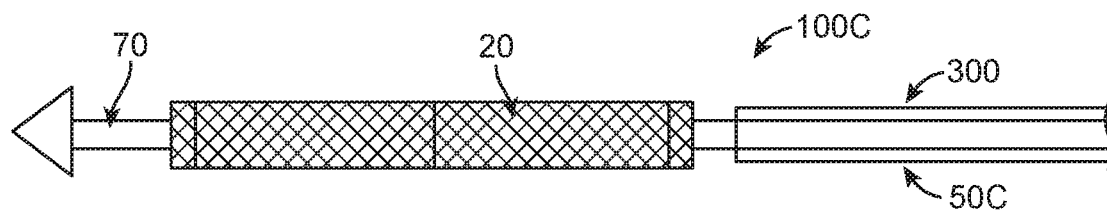
FIG. 17B is a simplified side view of the system of FIG. 17A and illustrating the outer sheath in a retracted position.
Figure 17C:
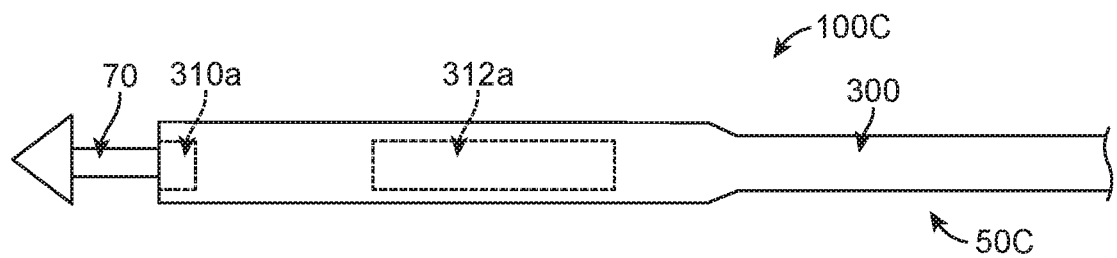
FIG. 17C is a simplified side view of the system of FIG. 17A and illustrating the outer sheath recapturing the stented prosthetic heart valve.

Once the stented prosthetic heart valve 20 is desirably located, the outer sheath 300 is retracted from over the prosthesis 20. Tension in the cords 62a-62c is then slowly released as described above, allowing the prosthesis 20 to self-revert toward the normal, expanded condition. Prior to completely releasing the cords 62a-62c from the stented prosthetic heart valve 20, the clinician may desire to re-position the prosthesis 20 relative to the native anatomy or remove the prosthesis 20 from the patient. Under these and other circumstances, tension is re-applied to the cords 62a-62c, causing the stented prosthetic heart valve 20 to collapse back on to the spindle 70. It may be difficult to fully collapse the prosthesis 20 in situ using only the cords 62a-62c. FIG. 17B reflects this possibility, with the prosthesis 20 slightly expanded relative to the spindle 70. The outer sheath 300 can then be distally advanced back over the partially expanded stented prosthetic heart valve 20 to assist in recapture, as shown in FIG. 17C. In this regard, the outer sheath 300 readily diametrically stretches or expands in the regions of the windows 310a-312b (two of which are generally identified in the view) to accommodate the slightly enlarged outer diameter of the partially expanded stented prosthetic heart valve 20 (as compared to the outer diameter of the prosthesis in the delivery state (FIG. 17A)).

Although the present disclosure has been described with reference to preferred embodiments, workers skilled in the art will recognize that changes can be made in form and detail without departing from the spirit and scope of the present disclosure.

What is claimed is:

1. A delivery device for delivering a stented prosthetic heart valve including a valve structure carried by a stent frame configured to self-expand from a collapsed condition to a normal, expanded condition, the delivery device comprising:
    an inner shaft forming a lumen;
    a spindle associated with the inner shaft; and
    a covering feature associated with the spindle for selectively covering at least a portion of a stented prosthetic heart valve positioned over the spindle in a delivery state; the covering feature having a proximal end and a distal end; wherein the covering feature includes a tip mounted to the spindle; wherein the tip defines a tip region, a transition region and an overhang region, the overhang region defining an inversion section adjacent the transition region and a cover section at the proximal end, the transition region having an outer diameter that is less than an outer diameter of the cover section, wherein the tip region defines a radial shoulder at the transition region; and further wherein the overhang region is configured to transition from a normal arrangement in which the cover section is not positioned over the transition region to an inverted arrangement in which the inversion section is folded so that the cover section is positioned over the transition region, wherein the inversion section terminates proximal to the radial shoulder in the inverted arrangement.

2. The delivery device of claim 1, wherein the overhang region is configured to cover a distal portion of the stented prosthetic heart valve in the delivery state.

3. The delivery device of claim 2, wherein the overhang region extends proximally from the transition region in the normal arrangement of the tip.

4. The delivery device of claim 3, wherein the overhang region defines a first inner diameter in the normal arrangement; wherein the tip is configured to be transitionable from the normal arrangement to a deflected arrangement in which the overhang region defines a second inner diameter, the second inner diameter being greater than the first inner diameter.

5. The delivery device of claim 1, wherein the overhang region has a variable wall thickness.

6. The delivery device of claim 1, wherein the tip is an integral, homogeneous body.

7. The delivery device of claim 1, wherein the transition region is positioned between the tip region and the overhang region; wherein a central passage extends through the tip region, transition region and the overhang region.

8. The delivery device of claim 7, wherein the central passage defines a lip in the tip region; wherein the spindle abuts the lip.

9. The delivery device of claim 1, wherein the inversion section has an increasing outer diameter from the transition region to the cover section.

10. The delivery device of claim 1, wherein the covering feature is an integral, homogenous body.

11. The delivery device of claim 1, wherein a central passage continuously extends from the proximal end to the distal end and a shape of the central passage is defined by the tip region, the transition region and the overhang region.

12. A delivery device for delivering a stented prosthetic heart valve including a valve structure carried by a stent frame configured to self-expand from a collapsed condition to a normal, expanded condition, the delivery device comprising:
    an inner shaft forming a lumen;
    a spindle associated with the inner shaft, wherein the spindle defines a first hole open to the lumen and an exterior of the spindle;
    a first cord slidably disposed within the lumen for selectively compressing a stented prosthetic heart valve; and
    a covering feature associated with the spindle for selectively covering at least a portion of a stented prosthetic heart valve tethered to the spindle in a delivery state;

the covering feature having a proximal end and a distal end; wherein the covering feature includes a tip mounted to the spindle; wherein the tip defines a tip region having a radial shoulder, a transition region and an overhang region, the overhang region defining an inversion section adjacent the transition region and a cover section at the proximal end, the transition region having an outer diameter that is less than an outer diameter of the cover section; wherein the inversion section has an inverted arrangement in which the inversion section is positioned over the transition section and terminates proximal to the radial shoulder.

13. The delivery device of claim 12, wherein a central passage continuously extends from the proximal end to the distal end and a shape of the central passage is defined by the tip region, the transition region and the overhang region.

14. The delivery device of claim 13, wherein the central passage defines a lip in the tip region; wherein the spindle abuts the lip.

* * * * *